(12) United States Patent
Johnson et al.

(10) Patent No.: US 7,910,002 B2
(45) Date of Patent: *Mar. 22, 2011

(54) SEPARATION

(75) Inventors: Bo Johnson, Meersburg (DE); Lenart Lunggren, Lund (SE)

(73) Assignee: Alteco Medical AB, Lund (SE)

( * ) Notice: Subject to any disclaimer, the term of this patent is extended or adjusted under 35 U.S.C. 154(b) by 361 days.

This patent is subject to a terminal disclaimer.

(21) Appl. No.: 12/036,603

(22) Filed: Feb. 25, 2008

(65) Prior Publication Data

US 2008/0203021 A1    Aug. 28, 2008

Related U.S. Application Data

(62) Division of application No. 11/491,886, filed on Jul. 24, 2006, now Pat. No. 7,601,134, which is a division of application No. 10/409,732, filed on Apr. 9, 2003, now abandoned.

(30) Foreign Application Priority Data

Apr. 25, 2002 (SE) ...................................... 0201257

(51) Int. Cl.
B01D 61/00 (2006.01)
B01D 29/00 (2006.01)
B01D 29/56 (2006.01)

(52) U.S. Cl. ........ 210/650; 210/348; 210/488; 210/489; 210/490; 210/502.1; 210/503; 210/504; 210/506; 210/649; 210/651

(58) Field of Classification Search ............... 210/645, 210/649, 650, 651, 660, 252, 348, 488, 489, 210/490, 502.1, 503, 504, 506; 422/44; 530/413, 415, 416, 417

See application file for complete search history.

(56) References Cited

U.S. PATENT DOCUMENTS

| 3,994,799 | A |   | 11/1976 | Yao et al. |
| 5,153,166 | A | * | 10/1992 | Jain et al. ...................... 502/402 |
| 5,567,615 | A | * | 10/1996 | Degen et al. .................. 435/280 |
| 5,855,782 | A |   | 1/1999 | Falkenhagen et al. |
| 5,989,420 | A |   | 11/1999 | Sugimoto |
| 6,022,477 | A |   | 2/2000 | Luo et al. |
| 6,408,894 | B1 |   | 6/2002 | Davankov |
| 6,497,675 | B1 |   | 12/2002 | Davankov |
| 6,616,623 | B1 |   | 9/2003 | Kutushov |
| 6,635,174 | B1 | * | 10/2003 | Berg et al. .................. 210/198.2 |
| 2002/0115225 | A1 | * | 8/2002 | Wagner et al. ................ 436/518 |

FOREIGN PATENT DOCUMENTS

| EP | 0 424 698 | 5/1991 |
| EP | 0 464 872 | 1/1992 |
| EP | 0 679 436 | 11/1995 |
| JP | 01-119264 | 5/1989 |
| WO | WO 00/62836 | 10/2000 |
| WO | WO 01/23413 | 4/2001 |

* cited by examiner

*Primary Examiner* — John Kim
(74) *Attorney, Agent, or Firm* — Merchant & Gould P.C.

(57) ABSTRACT

The invention refers to method for selectively binding and separating at least one component from whole blood or a body fluid, whereby the blood or body fluid is allowed to pass through a rigid integral separation matrix without being excluded therefrom. The matrix has a porous structure with a pore size ranging from 5 micron to 500 micron as well as an active surface ranging from 0.5 cm$^2$ to 10 m$^2$, and the surface is able to bind such components.

17 Claims, 4 Drawing Sheets

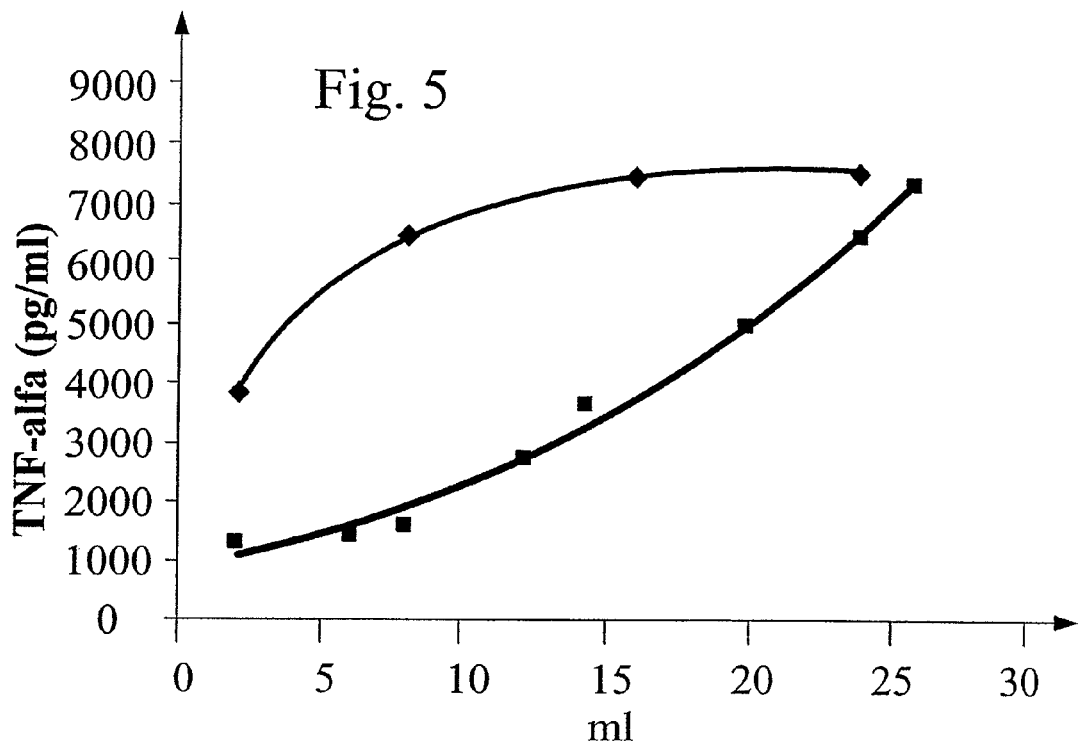
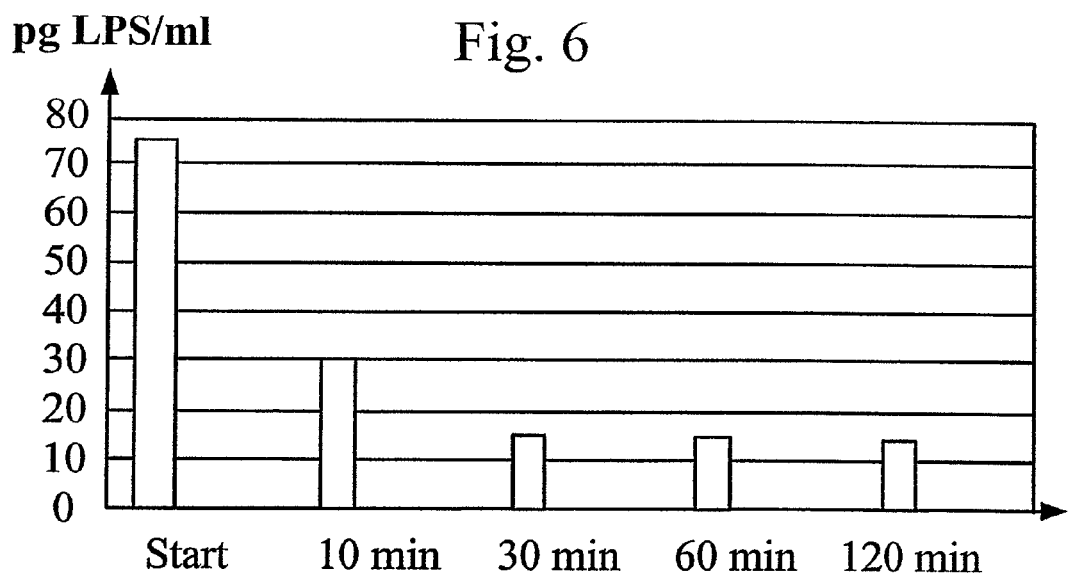

SEPARATION

This application is a divisional of U.S. application Ser. No. 11/491,886, filed Jul. 24, 2006, which issued as U.S. Pat. No. 7,601,134 on Oct. 13, 2009, which is a divisional of Ser. No. 10/409,732, filed Apr. 9, 2003, now abandoned. The entire disclosure of the U.S. application Ser. No. 11/491,886 and 10/409,732 are incorporated herein by reference, a claim of priority to each is made to the extent appropriate.

The present invention relates to improvements in removal of components from whole blood or a body fluid. More specifically, the invention relates to a method, wherein blood or body fluid is allowed to pass through a rigid integral separation matrix without being excluded therefrom.

BACKGROUND

Inflammatoric processes, such as sepsis, are a major cause of morbidity and mortality in humans. It is estimated that, yearly, 400 000 to 500 000 episodes of sepsis results in 100 000 to 175 000 human deaths in the U.S. alone. In Germany, sepsis rates of up to 19% of patients stationed at Intensive Care Units have been noted. Sepsis has also become the leading cause of death in intensive care units among patients with non-traumatic illnesses. Despite the major advances of the past decades in the treatment of serious infections, the incidence and mortality due to sepsis continues to rise.

There are three major types of sepsis characterized by the type of infecting organism. Gram-negative sepsis is the most common. The majority of these infections are caused by *Esherichia coli, Klebsiella pneumoniae* and *Pseudomonas aeruginosa*. Gram-positive pathogens, such as the staphylococci and the streptococci, are the second major cause of sepsis. The third major group includes the fungi. Fungal infections constitute a relatively small percentage of the sepsis cases, but they result in a high mortality rate.

A well-established mechanism in sepsis is related to the toxic components of gram-negative bacteria, i.e. the lipopolysaccharide cell wall structure (LPS, endotoxin), which is composed of a fatty acid group, a phosphate group, and a carbohydrate chain.

Several of the host responses to endotoxins have been identified, such as release of cytokines, which are produced locally. In case of an extensive stimulation, however, there is a spill over to the peripheral blood and potential harmful effects are obtained, such as induced organ dysfunction.

The key mediators of septic shock are Tumor Necrosis Factor (TNF-$\alpha$), Interleukine 1 (Il-1) and Interleukine 17 (Il-17), which are released by monocytes and macrophages. They act synergistically causing a cascade of physiological changes leading to circulation collapse and multi organ failure. Indeed, high concentrations of TNF-$\alpha$ can mimic the symptoms and outcome of sepsis.

Normally, endotoxins are kept within the lumen of the intestine. For example, during cardiopulmonary bypass the presence of splanchic ischemia or dysoxia causes disruption of the mucosal barrier and translocation (i.e. the transport of endotoxins from the intestine to the circulation system) of endotoxins from the gut lumen to the portal circulation.

Antibiotics of varying types are widely used to prevent and treat infections. However, for many commonly used antibiotics an antibiotic resistance is developed among various species of bacteria. This is particularly true for the microbial flora resident in hospitals, where organisms are under a constant selective pressure to develop resistance. Furthermore, in the hospital the high density of potentially infected patients and the extent of staff-to-staff and staff-to-patient contact facilitate the spreading of antibiotic resistant organisms. The antibiotics used are the most economical, the safest and the most easy to administer and may not have a broad enough spectrum to suppress certain infections. Antibiotics can be toxic to varying degrees by causing allergy, interactions with other drugs, and causing direct damage to major organs (e.g. liver, kidney). Many antibiotics also change the normal intestinal flora, which can cause diarrhea and nutritional malabsorption.

Certain antibiotics are known to neutralize the action of endotoxins, such as polymyxin B. This antibiotic binds to the lipid A part of endotoxin and neutralizes its activity. Polymyxin is not used routinely due to its toxicity. It is only given to patients under constant supervision and monitoring of the renal function.

Furthermore, in order to overcome some of the limitations inherent to active immunization against bacterial components, various techniques have been used to produce endotoxin-binding antibodies. A large number of antibodies have been prepared by immunization of humans with bacteria.

In order to develop more consistent preparations of therapeutic antibodies, numerous LPS-reactive monoclonal antibodies have been developed. Unfortunately, the clinical studies have not resulted in benefits. However, it should be noted that these trials were performed in humans after onset of symptoms of sepsis. It is widely believed that an anti-endotoxin antibody treatment, administered after sepsis, may yield little benefit because these antibodies cannot reverse the inflammatory cascade initiated by the endotoxin.

In JP 06022633, an adsorbent for anti-lipid anti-bodies is shown, which comprises a compound with an anionic functional group immobilized onto a water-insoluble porous material. The porous material can be agarose, cellulose, dextran, polyacrylamide, glass, silica gel, or a hard polymer made of a styrene-divinylbenzene copolymer, and the porous material is packed as a bed of separate particles in a separation device.

In attempts to remove components from blood, different adsorbent materials have been prepared. An endotoxin removal adsorbent comprising a ligand immobilized on a solid phase support medium is shown in WO 01/23413. A preferred support medium is in the form of beads. When packed in a separation device, the solid phase support medium is porous enough to allow passage of blood cells between the beads.

In WO 00/62836, the adsorbent material has a size and a structure adapted to remove $\beta$-2 microglobulin from blood. The adsorbent material of this document can be a macroporous synthetic polymer with a surface of beads and of pores modified as to prevent adsorption of proteins and plateletes. However, individual spherical beads of the polymer were mechanically destroyed at a loading of about 500 g, which is obtained in for example a column packed with the beads. Such a loading results in a considerable pressure drop over of the column.

In order to reduce the pressure drop, an absorbent has been prepared in EP 464872, which comprises water-insoluble porous hard gel particles having an exclusion limit of $10^6$-$10^9$ Dalton. The gel bed is used for selective removal of lipoproteins from blood or plasma in extracorporeal circulation treatment.

Likewise, in WO 01/23413 the porous support material for endotoxin removal is beads, which can be filled into a container, the beads having a size sufficient to provide the requisite space between the beads when packed into a column or filter bed. The porous support material can also be microfiltration hollow-fibers or flat sheet membranes in order to minimize pressure drops.

In EP 424698 an adsorbent for eliminating biomacromolecules is shown, which consists of a carrier of porous spherical particles having a particle size of 50-150 microns and an exclusion limit of at least $10^5$ Dalton. Polymyxin B is coupled to the particles, which are subsequently filled in a cartridge to be used in a system for extracorporeal endotoxin removal from whole blood.

In these traditional systems for extracorporeal removal of toxic components from blood, a container or cartridge is first filled with a liquid and the adsorbing porous beads are introduced afterwards. In U.S. Pat. No. 6,408,894 a method is shown, which provides a more uniform distribution and denser packing of the beads. The method involves forcedly supplying a mixture of liquid and beads into a container in such a manner that the liquid is squeezed out of the mixture and out of the container.

Thus, an elimination of blood cells facilitates the removal of compounds present in plasma as described above, e.g. in WO 00/62836 or WO 01/23413. However, such a technique involves two separation steps which both could contribute to an enhanced risk of adverse cellular activation due to bioincompatability.

SUMMARY

The purpose of the present invention is to provide a new method for selective binding and separating at least one component from whole blood or body fluids, whereby the above mentioned problems in connection with inflammatoric processes are eliminated.

Another purpose is to provide such a method, whereby the selective binding and separation can be accomplished on whole blood without the need of separating blood into plasma and blood cells.

A further purpose of the invention is to provide such a method, which is not size-dependent, i.e. the blood components are not separated by means of exclusion.

Still another object of the invention is to provide such a method, whereby high flow rates can be obtained in a separation device without significant pressure drop with time.

Yet a further purpose is to provide such a method without subjecting the blood to shear forces in a separation device even at very high flow rates while maintaining a low line pressure in order to avoid damage to bloodvessels.

BRIEF DESCRIPTION OF THE DRAWINGS

FIG. 5 is a graphic representation of data obtained according to example 32.

FIG. 6 is a graphic representation of data obtained according to example 33.

DETAILED DESCRIPTION

Figure 1:
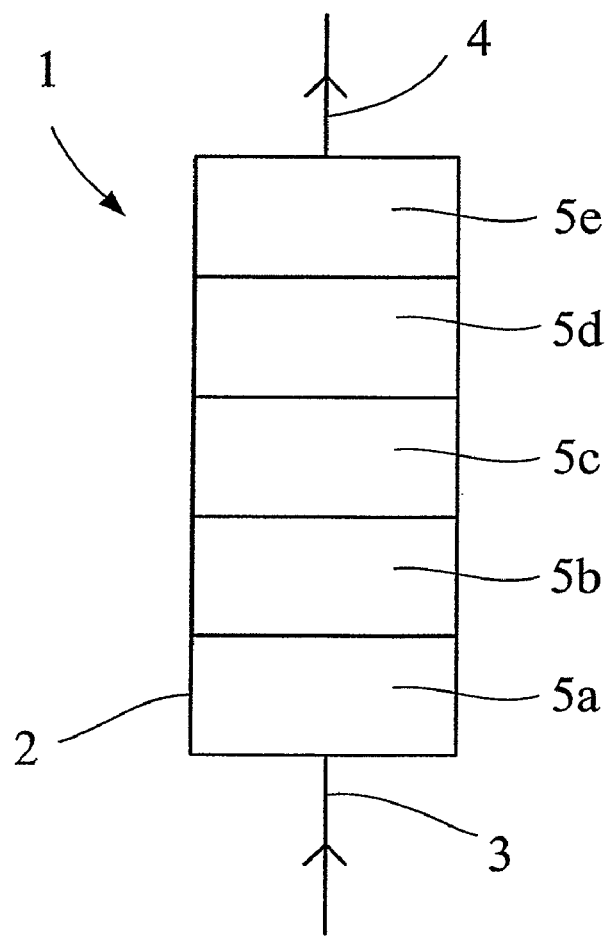
FIG. 1 is a schematic representation of a device for selectively binding and separating at least one component from a body fluid.

According to the invention, a method is provided for selectively binding and separating at least one component from whole blood or a body fluid. The blood or body fluid is allowed to pass through a rigid integral separation matrix without being excluded therefrom, the matrix having a porous structure with a pore size ranging from 5 micron to 500 micron and an active surface ranging from 0.5 $cm^2$ to 10 $m^2$, which is able to bind one or several components.

In a preferred embodiment of the invention the matrix further comprises at least one functional group which has been introduced by means of coating and/or surface modification of the porous structure. This results in that the active surface obtained, alone or in combination with non-functionalized regions of the same, is able to selectively bind at least one component of whole blood or a body fluid. The components to be removed can be natural as well as non-natural, i.e. a specific ligand, such as an antibody, is attached to the component.

Furthermore, the functional groups, obtained by means of direct or indirect selective conversion of the surface of the porous structure, have been further used for immobilization of ligands. However, the functional groups of the porous structure can be utilized as they are in the inventive method.

The pore size as well as the surface of the skeletal-like porous structure has been adapted to be used in the separation matrix of the inventive method in connection with whole blood purification. However, the method according to the invention can also be used for the removal of components from other body fluids as well as aqueous solutions. It is an important aspect of the invention that neither any component nor any solvent is excluded from the matrix during a separation procedure.

According to the invention, the rigid integral matrix should have an available surface from 0.5 $cm^2$ to 10 $m^2$, and the density of the matrix structure is not limiting for performing the inventive method.

In this connection the term "rigid" means that the matrix is not flexible, not bending or yielding, but able to withstand a pressure of at least 0.5 bar. The term "integral" means that the matrix with high surface area is an entire entity.

The porous structure of the matrix in the inventive method is made of metal, inorganic oxide, carbon, glass, ceramic, synthetic polymer, and/or natural polymer, or mixtures thereof. Porous solid metal structures with well-defined pore sizes and high surface areas can be manufactured by using strictly controlled sintering processes that produces uniformly-sized pores.

Different polymers have been produced as a moulded or extruded porous material with a porous structure, having the desired pore size as well a high surface area for the matrix. They have also been produced as foam. For example, polyurethanes prepared from isocyanates and various other organic compounds have active hydrogen atoms, which have been used for producing poly-addition products. This active hydrogen can come from bifunctional or polyfunctional compounds, such as polyalcohols, polyamines. Reactions with water gives rise to primary amines which have been used for covalent immobilization of specific ligands.

A wide variety of metals and alloys have been used, such as stainless steel, nickel, titanium, monel, inconel, hastelloy and other special metal materials. High surface area inorganic oxides, especially alumina and zirconia, have also been utilized with the same techniques to produce ceramic materials with defined pore structures. Likewise, such ceramics as well as sintered glass can be purchased, which have adequate pore sizes.

Other natural rigid materials, such as amorphous silica, e.g. zeolites, and lava rock, have also been used.

Natural materials and hybrides thereof, which can be used as a matrix material in the inventive method, are polysaccharides, such as cellulose, and other polymeric carbohydrate materials. Other suitable natural polymeric materials are polyamino acids, also those involving synthetic amino acids, polylactic acid, polyglycolic acid and its copolymers with lactic acid.

In this connection the term hybrid encompasses derivatives of such natural materials, for example cellulose diacetate, which is a preferred polysaccharide derivative.

Suitable synthetic polymers for the matrix to be used in the present invention are polyolefines, such as polyethylene, polypropylene, polybutylene, polymethylpentene, and ethylene vinyl acetate copolymers; vinylic polymers, such as polyvinyl alcohol, polyvinyl acetals, and polyvinylpyrrolidone; fluorine containing polymers, such as polytetrafluoroethylene, fluorinated ethylene-propylene copolymer, polychlorofluoroethylene, polyvinylfluoride, and polyvinylidene fluoride; polyacrylates, such as polymethylmethacrylate, cyanoacrylate, polyacrylonitrile, and polymethacrylates; polyamides, such as polyacrylamide; polyimides, such as polyethylenimines; polystyrene and its copolymers, such as polystyrene and acrylonitrilebutadiene-styrene-polymers; silicone rubbers; polyesters/ethers; polycarbonates; polyurethanes; polysulfonates; polyglycols; polyalkyloxide such as polyethyleneoxide, polypropyleneoxide; and copolymers or hybrids thereof.

In the preferred embodiment, at least one functional group has been introduced onto a porous structure of the rigid integral separation matrix. The functional groups can be of different kinds, i.e. of the anionic, cationic or nonionic type. The functional groups of the porous structure have been used to covalent bind substances like peptides/proteins and bile acids (e.g. deoxycholic acid), antibodies and fragments thereof as well as other biomolecules and substances having the ability to selectively bind endotoxins and/or proinflammatory mediators.

A surface modification, i.e. a surface functionalization in an indirect way, was accomplished by means of electro-deposition, electro-evaporation, plasma chemical deposition, deposition from an ion plasma flow, or chemical vapor deposition (e.g. plasma polymerization, plasma enhanced surface polymer deposition). The surface modification methods are known per se and found in "Plasma surface modification and plasma polymerization" by N. Inagaki, 1996, Technomic Publishing, Lancaster, USA. Different three-dimensional matrix structures have been treated by means of these methods, a very homogeneous modification of the active surface being achieved.

Polymerization of bifunctional monomers of acrylic or allylic double bonds with polar groups as OH, $NH_2$, CN and COOH have been used to produce plasma polymers with high density of the functional groups. For example, surface functionalization of the inorganic and organic surfaces have been carried out in a plasma environment of allyl compounds, such as allylamine.

It has also been possible to organic polymeric surfaces in $NH_3$, $O_2$, or $CO_2$ plasma environments, which give rise to either of the functional groups =NH, —$NH_2$, =CN, —OH, or —COOH. Other examples of gases used are well-known within the art.

A plasmachemical processing have also been combined with classic chemical synthesis, the selectivity of surface modifications for polymers being significantly enhanced.

One approach has been to apply a specific plasma gas surface functionalization immediately followed by a chemical unification of the coexisting plasma functional groups.

Another way of introducing the functional groups is by means of a direct functionalization, i.e. coating the surface with a polymeric material. In this connection the synthetic or natural polymer has been coated onto the high surface metal, inorganic oxide, carbon, glass, ceramic, as well as another suitable synthetic polymer, and/or a natural polymer, or mixtures thereof.

Many of the above-mentioned polymers, especially those without functional groups, such as polyethylene, polypropylene, polytetrafluoroethylene etc., need a further treatment in order to alter their surface properties. Thus, a plasma or corona treatment, as mentioned above, of the polymer surface will generate a very unique functional group, like hydroxyl, carbonyl, carboxyl, amino, and imino groups etc, which are covalently attached to the surface. The coating has also been accomplished by means of adhesion or adsorption of a polymeric substance having functional groups. Examples of such substances are polylysine, polyarginine, and polyethyleneimine.

By for example using a plasma technique, polyethyleneimine-like substances was obtained on the porous surface. When a separation matrix is used in the method according to the invention for selectively binding and separating at least one component from whole blood or a body fluid, the hydrophilic as well as the hydrophobic regions of proteineous blood components can interact with the processed surface in order to remove the desired components. After functionalization, when the matrix surface for selective binding and separation comprises a polyolefine, e.g. a polyethylene or polypropylene, the positive charges of the amino groups are likewise used for electrostatic interactions and the hydrophobic regions are used for hydrophobic interactions. This approach is used in the inventive method for the selective binding of different regions of for example lipopolysaccharides.

Polymers and metals, having for example reactive hydroxyls, can also be functionilized by means of silanization.

Accordingly, various different functional groups have been covalently coupled to the high surface porous matrix structure. After a direct and/or indirect functionalization, the porous structure can have hydrophilic as well as hydrophobic regions, which can interact the different blood components. Thus, the characteristic properties of a substance of interest are utilized when preparing the surface to be used in the method according to the invention.

Preferably, the functional groups of the active surface are sulfhydryls, carboxylates, amines, aldehydes, ketones, hydroxyls, halogens, hydrazides, and active hydrogen.

In another preferred embodiment, a ligand has been coupled to the at least one functional group of the high surface porous structure in a covalent way. In this connection, a ligand is a substance with high affinity for the component to be removed from whole blood or a body fluid. Thus, the ligand is used to enhance the adsorption properties and the efficacy of binding.

The ligand can be a protein, preferably a recombinant protein, a peptide, an antibody or a fragment thereof, a carbohydrate, e.g. a polysaccharide, a hormone, an antioxidant, a glycoprotein, a lipoprotein, a lipid, a fat soluble vitamin, e.g. vitamin E, a bile acid, a reactive dye, allantoin, uric acid, or polymyxin, or combinations thereof.

A suitable bile acid is deoxycholic acid, which is an endogenous hydrophobic substance. Such a bile acid can be coupled either directly to the functional groups, via a spacer, or coupled via a large molecule, and is then used for removing endotoxins from blood, body fluids and aqueous solutions as in the method according to the invention.

In this connection a spacer is a molecule, large or small, which connects the ligand to the surface of the porous structure.

For example, if in the inventive method the porous structure of the separation matrix comprises a polyolefine having an added amine-group, this group can have an albumin coupled thereto and in turn at least one a bile acid moiety coupled to this large molecule.

Thus, the invention also refers to a new use of a bile acid moiety immobilized on a support for eliminating a component from an aqueous solution comprising the same. Preferably, the bile acid moiety is a deoxycholic acid moiety.

Accordingly, a suitable solid support for immobilization of the bile acid moiety is a rigid integral separation matrix having a porous structure with a pore size ranging from 5 micron to 500 micron, preferably from 70 micron to 170 micron, and an active surface ranging from $0.5$ $cm^2$ to $10$ $m^2$.

It is also preferred that the ligand of the matrix in the inventive method is albumin or an albumin produced by means of recombinant technology, which can be used instead of serum albumin, polymyxin B (i.e. charged groups on a hydrophobic structure), or deoxycholic acid.

Thus, a ligand can also act as a spacer in the method according to the invention. For example, it has also been possible to first covalently attach a human recombinant protein or another large molecule (e.g. hyaluronic acid) to the porous structure, which allows for a subsequent binding of the ligand specific for the component to be removed.

If necessary, a crosslinker is coupled between the at least one functional group and the ligand in a covalent way. In this connection, a cross-linker is an element that covalently bonds the ligand to the supportive porous structure, the element being a spacer when linking the ligand at a distance from the porous structure itself. Such molecular spacers are known within the art. They have been introduced in order to increase the affinity for the component to be bound and separated from whole blood or body fluids by providing a better availability to the ligands. The biocompatibility of the surface of the porous matrix structure is also increased by the introduction of these molecular spacers.

A crosslinker/spacer can comprise a zero-length crosslinker alone or in a combination with an intervening crosslinker, the final complex obtained being bound together by virtue of chemical substances that add structures to the crosslinked substance. These intervening crosslinkers can be of type homobifunctional (e.g. dialdehydes), heterobifuntional (e.g. amino acids) or trifunctional crosslinking type.

The main purpose of the spacer is to increase the bioavailability of the specific ligand used.

The spacer can for example be a silane, a diisocyanate, a glycolate, a polyethyleneglycol, a succinimidyl reagent, a dihydrazine, adipidic acid, a diamine, an amino acid, a poly or oligo amino acid, a polyamino acid, a peptide, or a protein. Preferably, the protein is a human recombinant protein.

The functional groups of the cross-linker are designed to react with amino groups (Lys, Arg), with sulfhydryls (Cys), or with carboxyls (Asp, Glu), to cite a few examples.

In connection with the chemistry of reactive groups, reference is made to Bioconjugate Techniques, Greg T Hermanson, Academic Press, USA 1996.

Thus, the active porous matrix surface is in the inventive method capable of removing for example endotoxins, alone or in combination with non-functionilized regions of the available surface of the porous structure. The active surface can also be used as a tool for covalent immobilization of chemicals, such as biomolecules like amino acids, polypeptides and antibodies in order to selectively enhance the elimination of such specific components.

A separation matrix, which is intended for selective removal of at least one component from whole blood or body fluids, can be produced with a porous structure of a certain pore size and/or a certain pore size range in dependence on the intended application. Preferably, the porous structure should permit passage of blood cells. Accordingly, certain types of blood cells can also be removed from whole blood by means of the inventive method. Such cells sick cells or cells with specific surface receptors, for example activated phagocyting cells.

The metal structure can for especial applications be magnetic. A magnetic matrix can for example be obtained by coating sintered magnetite with a polymer, e.g. polyethylene. An efficient removal of cells can then be performed allowing antibodies, having a magnetic dextran iron label, to attach to specific cells in the blood.

The pore size should be within the range from 5 micron to 500 micron, preferably from 70 micron to 170 micron, most preferred from 80 micron to 100 micron, so that high flow rates can be maintained without cellular damage or cellular exclusion. Thus, the separation accomplished with the method according to the invention is not based on any size distribution of components. Virtually all components of whole blood or a body fluid might be eliminated by means of the inventive method.

After the removal of one or more primary toxic effectors, i.e. an endotoxin, further secondary toxic effectors can be removed. The secondary effectors can be cytokines (e.g. TNF-α), interleukines (e.g. Il-1), reactive oxygen and nitrogen radicals, etc.

When performing the method according to the invention, one or several separation matrixes are protected within a housing, which can have various shapes and varying and/or different in- and outlets depending on the application. Such a device can then be used for endotoxin removal and/or cytokine removal and/or cytokine neutralization. This is accomplished by passing blood or other body fluids through the device, applied intra, para, or extracorporally, without the liquid being excluded from the rigid integral separation matrix therein. The active surface of the porous structure, the functional groups and/or specific ligands thereon then selectively binds and separates at least one component from the liquid. The device can advantageously also be used for removal of endotoxins from aqueous solutions.

An important feature of the inventive method is that all aspects of septic shock can be provided for, i.e. primary as well as secondary toxic effectors can be removed by means of the inventive method.

Reference is made to FIG. 1 in connection with performing the method according to the invention. A device 1 comprises a housing 2, the housing (or cartridge) of the device being integrated into a closed circulation, in which whole blood or body fluids is circulated by means of a pump. In the housing 2 at least one separation matrix 5a, 5b, . . . is arranged, each intended to selectively remove one component from whole blood or body fluids. The housing 2 is provided with an inlet 3 and an outlet 4, the sites of which are of no importance as long as an adequate flow is obtained within the separation matrix(es) and the housing. Preferably, the pump is arranged upstream the inlet 3.

In this way a device is obtained which can maintain flow rates from 5 ml/h to 6 000 ml/min without a significant pressure drop. When applied extracorporeally, a line pressure of not more than 300 mm Hg from pump to cannula is obtained even at very high flow rates.

The rigid integral separation matrix can be produced in different shapes to be used in the inventive method. It can for example be designed as a disk, a rod, a cylinder, a ring, a sphere, a tube, a hollow tube, a flat sheet, or other moulded shapes.

Since the flow within each separation matrix is dependent on its porosity, the contact time of the components in blood or a body fluid with the active surface can be controlled. Furthermore, a desired flow gradient can be created within a separation device by changing the porosity and configuration of the individual separation matrixes therein.

Figure 2:
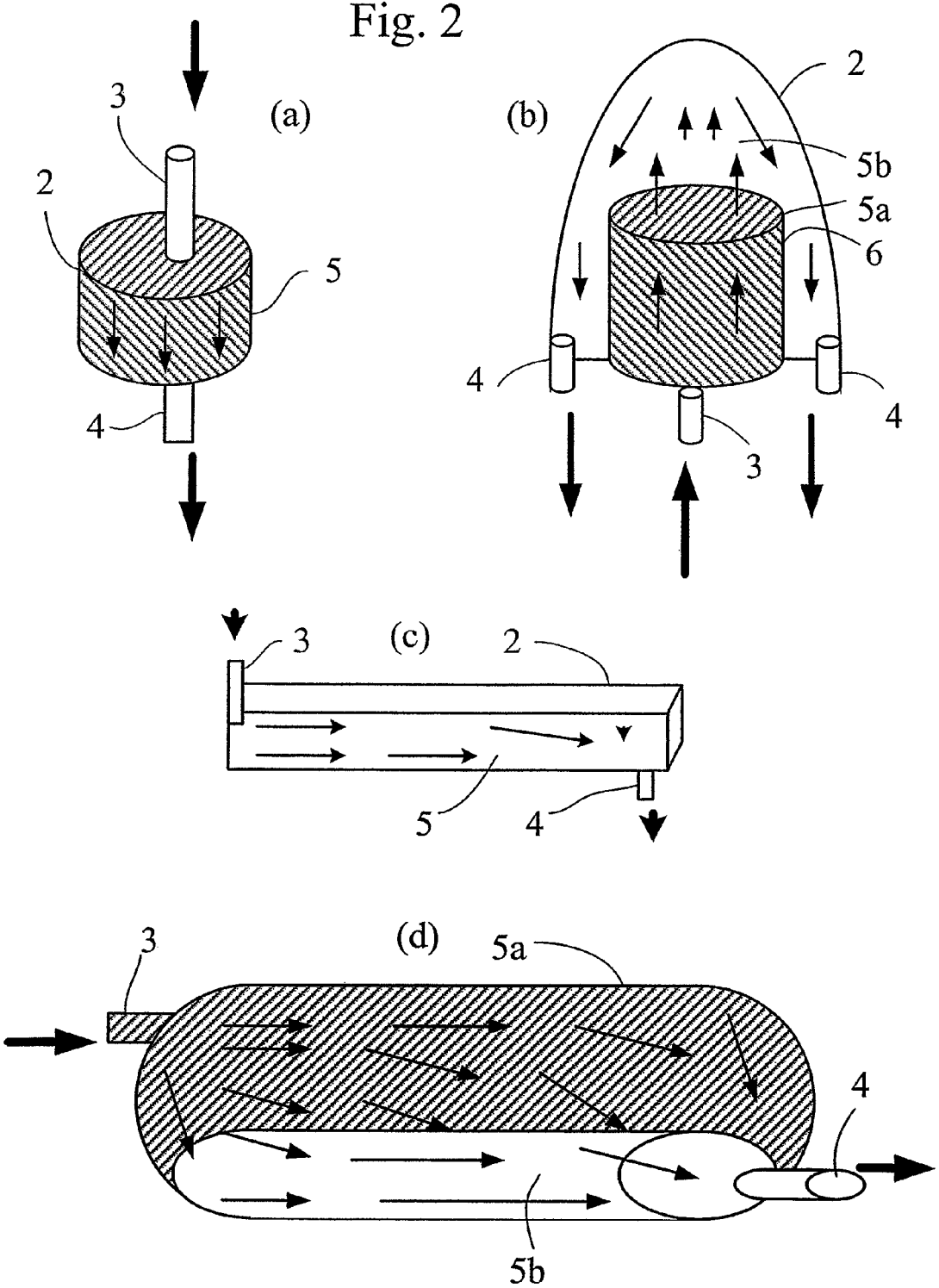
FIGS. 2(a)-(d) are schematic representations showing operation of the device of FIG. 1.
Figure 3:
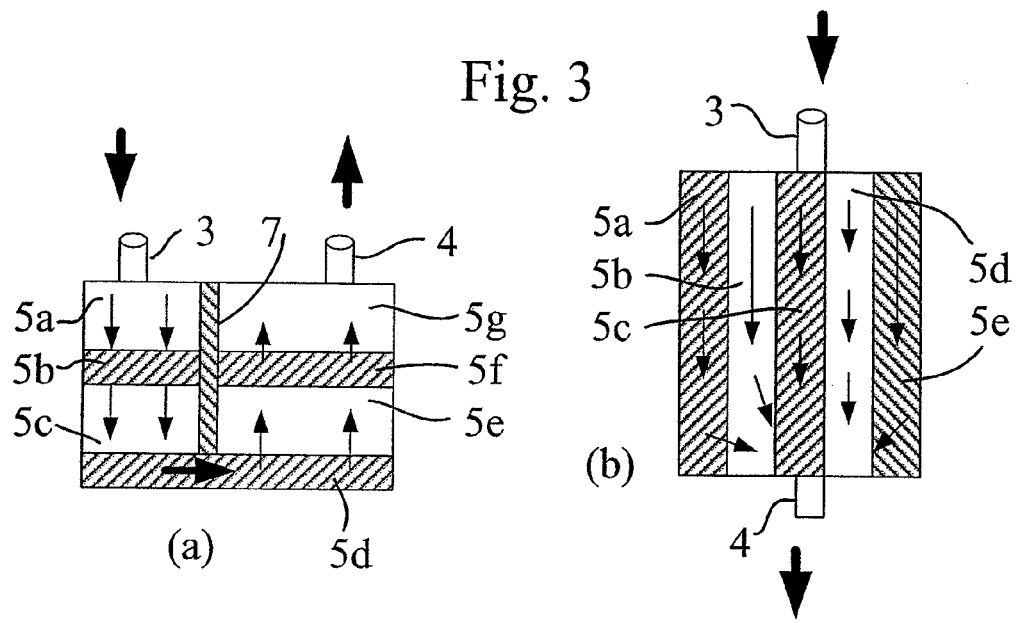
FIGS. 3(a)-(d) are schematic representations showing operation of the device of FIG. 1.
Figure 3:
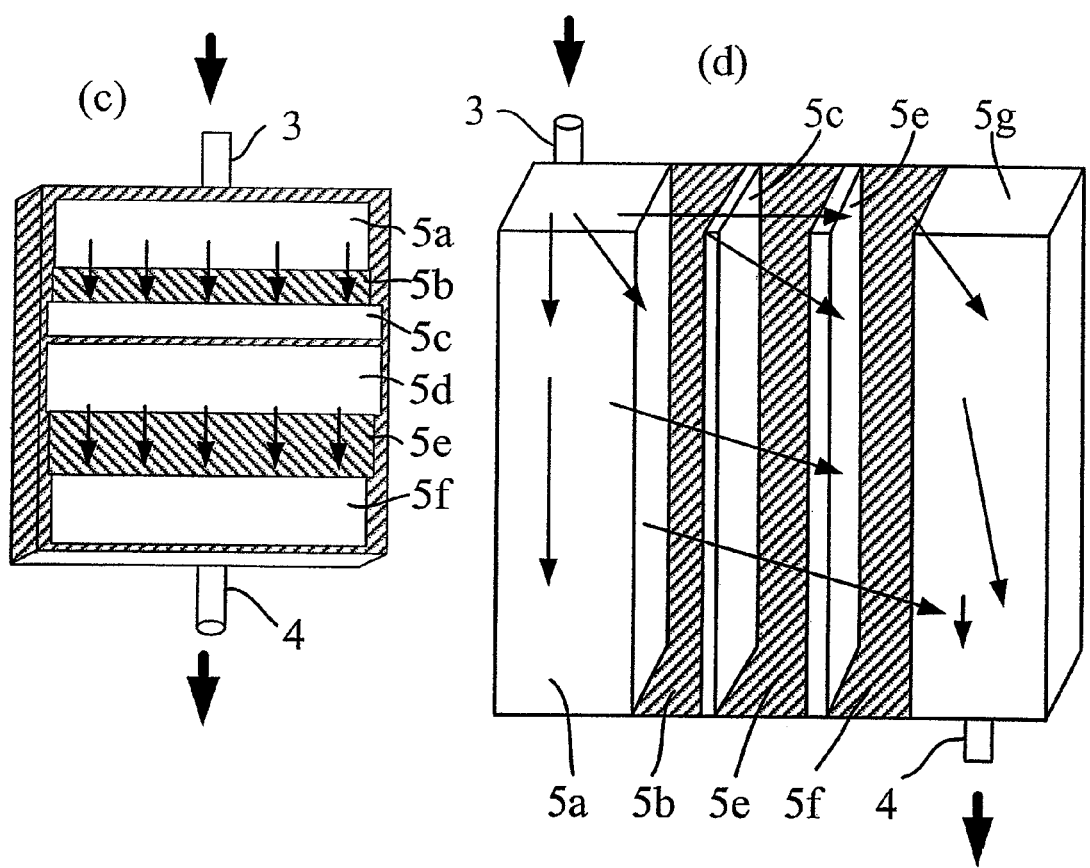

In FIG. 2 and FIG. 3 different schematic embodiments of devices are shown, which can be used when performing the method according to the invention. Arrows indicate the flow of blood or body fluid within the individual separation matrixes and the housings therefor, large arrows indicating a higher flow rate than small arrows. In these examples of different configurations the separation matrixes can have the same or different porosities with or without the same or various types of functional groups or ligands in order to remove one or several components from blood or a body fluid.

The separation matrixes are preferably integrated with the housings (each having an inlet 3 and an outlet 4) in order to ensure that no liquid or components therein are prevented from entering the matrix or matrixes, i.e. being excluded therefrom. In FIGS. 2 (a) and (b) examples of one separation matrix 5 within a housing 2 are given, the matrix being of different configurations. Examples of two separation matrixes 5a, 5b within a housing 2 are shown in FIGS. 2 (c) and (d). In the device of FIG. 2 (c) an impermeable coating 6, such as an applied skin, on the outside periphery of the separation matrix 5a ensures that all the material supplied to the device will pass this entire matrix. In the device of FIG. 2 (d), on the other hand, some of the material supplied will have a shorter residence time in the separation matrix 5a than in the separation matrix 5b, and vice versa.

In FIG. 3 each device comprises several separation matrixes 5a-5g. In FIG. 3 (a) a partition wall 7 ensures a flow through all matrixes. The separation matrixes can be positioned laterally or transversally relative to their longitudinal directions, as in FIGS. 3 (b) and (c), respectively. In FIG. 3 (d) the device comprises separation matrixes of different sizes.

In conclusion, the inventive method can be used with an intra, para, or extracorporeally applied or stand alone device, which is thereby capable of reducing circulating endotoxins and potential harmful pro inflammatory mediators, especially TNF-α, IL-1 and IL-17, preferably in blood. It is also possible to selective remove endotoxins from other aqueous solutions. The components are considered to bind to the active surface of the rigid integral separation matrix by means of adhesion.

EXAMPLES

The invention will now be further described and illustrated by reference to the following examples, which have been carefully selected in order to encompass the invention. Accordingly, they should not be construed as limiting the invention in any way.

Surface Modifications

Example 1

The surface of a matrix of porous polyethylene (Porex Technologies, Germany), having a porosity of 350 micron and an active surface of 10 cm$^2$, was modified by means of plasma enhanced chemical vapour deposition by using $O_2$ (Plasma Science, USA, Type PS 0350 Plasma Surface Treatment System).

The formation of hydroxyl groups on the porous structure surface of the obtained matrix was assayed with a Dye test, the hydrophilicity thereof being confirmed.

Example 2

The surface of a matrix of porous polyethylene (Porex Technologies, Germany), having a porosity of 100 micron and an active surface of 20 cm$^2$, was modified by means of plasma enhanced chemical vapour deposition by using $CO_2$. (Plasma Science, USA, Type PS 0350 Plasma Surface Treatment System).

The formation of carboxyl groups and the amount on the porous structure surface of the obtained matrix was determined by conversion into hydroxamic acids. In this connection all hydroxamic acids give a red or violet color with ferric chloride in acid solution as described in Feigel et al.; Microchemie 15:18, 1934.

Example 3

The surface of a matrix of porous polyethylene (Porex Technologies, Germany), having a porosity of 170 micron and an active surface of 0.04 m$^2$, was modified by means of plasma polymerization by using allylamine (Plasma Science, USA, Type PS 0350 Plasma Surface Treatment System).

The amount of primary amines on the porous structure surface of the obtained matrix was determined by means of trinitrobenzene sulfonic acid (TNBS) assay.

Example 4

The surface of a matrix of porous polyethylene (Porex Technologies, Germany), having a porosity of 70 micron and an active surface of 0.26 m$^2$, was modified by means of plasma polymerization by using acrylic acid (Plasma Science, USA, Type PS 0350 Plasma Surface Treatment System).

The amount of carboxyl groups on the porous structure surface of the obtained matrix was assayed as described in Example 2.

Example 5

The surface of a matrix of porous polyethylene (Porex Technologies, Germany), having a porosity of 5 micron and an active surface of 0.9 m$^2$, was modified by means of plasma polymerization by using $NH_3$ (Plasma Science, USA, Type PS 0350 Plasma Surface Treatment System).

The amount of primary amines on the porous structure surface of the obtained matrix was assayed as described in Example 3.

Example 6

The surface of a matrix of porous polytetrafluorethylene, PTFE (W.L. Gore & Associates Inc., USA), having a porosity of 10 micron and an active surface of 100 cm$^2$, was modified by means of plasma enhanced chemical vapour deposition by using $NH_3$ (Plasma Science, USA, Type PS 0350 Plasma Surface Treatment System).

The amount of primary amines on the porous structure surface of the obtained matrix was assayed as described in Example 3.

Example 7

The surface of a matrix of porous, Polystyrene (Dow Chemical, USA), having a porosity of 10 micron and an active surface of 300 cm², was modified by means of plasma enhanced chemical vapour deposition by using $CO_2$ (Plasma Science, USA, Type PS 0350 Plasma Surface Treatment System).

The amount of carboxyl groups on the porous structure surface of the obtained matrix was assayed as described in Example 2.

Example 8

The surface of a matrix of porous polyurethane (Polymers Unlimited, Sweden), having a porosity of 80 micron and an active surface of 100 cm², was modified by means of a 2% solution of an Aldehydic Alkoxy Silane, Art No. (PSX 1050, United Chemical Technologies Inc., USA) in 95% ethanol. The pH of the solution was adjusted to pH 5.5 with acetic acid and the solution was perfused through the matrix, which was incubated over night at room temperature and then washed with 0.9% physiological saline.

The aldehyde functionality of the obtained matrix was evaluated by using a catalytic acceleration of the oxidation of p-phenylenediamine by hydrogen peroxide, p-phenylenediamine being oxidized by hydrogen peroxide in an acid solution, which is known as Bandrowski's base.

Example 9

The surface of a matrix of porous silicone (Nusil, France), having a porosity of 200 micron and an active surface of 0.5 m², was modified by means of a 2% solution of a Amine-Silane (Art No. 0750, United Chemical Technologies Inc., USA) in 95% ethanol. The solution was perfused through the matrix, which was incubated over night at room temperature and finally washed with 0.9% physiological saline.

The amount of primary amines on the porous structure surface of the obtained matrix was assayed as described in Example 3.

Coating by Means of Covalent Bonding

Example 10

Poly-Lysine (200 mg) was dissolved in 10 ml of 50 mM sodium carbonate solution and a matrix of porous polycarbonate with a porosity of 100 micron (MicroPore Plastics, USA) was then immersed into the solution and kept at 4° C. for 24 h in order to obtain a covalent bonding between the poly-lysine and the polycarbonate matrix. The porous matrix was finally washed with excess distilled water.

The amount of primary amines on the porous structure surface of the obtained matrix was assayed as described in Example 3.

Example 11

The porous polyethylene matrix obtained according to Example 4 was perfused with an aqueous solution of 1-cyclohexyl-3-(2-morpholinoethyl)carbodiimide metho-p-toluenesulfonate (WCCM) (Aldrich) at a flow rate of 5 ml/min in a closed circuit at room temperature for 6 h. Then it was rinsed with water and a solution of polyethyleneimine (Sigma) (10 mg/ml, pH 7.0) was finally added and the matrix was incubated over night.

The amount of primary amines on the porous structure surface of the obtained matrix was assayed as described in Example 3.

Example 12

The porous polyethylene matrix obtained according to Example 3 was conjugated by using 1.0% glutardialdehyde in 0.2 M phosphate buffer, pH 7.5, and perfused at a flow rate of 1 ml/min for 6 h at room temperature. The matrix was then washed with buffer before incubation with a hyaluronic acid solution (2 mg/ml) for 16 h at room temperature. Excess hyaluronic acid was finally rinsed off.

The hyaluronic acid content on the porous structure surface of the obtained matrix was verified and determined with Alcian Blue (Sigma).

Coating by Means of Adhesion

Example 13

A matrix of porous polyethylene (Porex Technologies, Germany), having a porosity of 70 micron and an active surface of 0.18 m², was perfused at a flow rate of 1 ml/min in a closed circuit for 16 h at room temperature with 2 mg/ml hyaluronic acid solution (BioHyos, Sweden, 12·10⁶ Da) at a pH of 3.3, which was adjusted with 0.1 M HCl.

The hyaluronic acid content on the porous structure surface of the obtained matrix was verified as in Example 12.

Example 14

A matrix of porous polyethylene (Porex Technologies, Germany), having a porosity of 70 micron and an active surface of 7.0 m², was placed in a glass tube. The tube, with the porous matrix therein, was filled with a solution of 0.13% poly-Lysine (Sigma) in 350 ml water, and the pH was adjusted to pH 3.3 with 0.1 M HCl. Then the solution of poly-lysine was recirculated through the tube with its filter matrix for 16 h at room temperature at a flow rate of <5 ml/min. The porous matrix was finally rinsed with reverse osmosis water.

The amount of primary amines on the porous structure surface of the obtained matrix was assayed as described in Example 3.

Example 15

A matrix of porous polyethylene (Porex Technologies, Germany), having a porosity of 70 micron and an active surface of 3.4 m², was placed in a glass tube. The tube with the porous matrix therein was filled with a 0.2% Recombumin™ (recombinant Human Serum Albumin, HoechstPharma, USA) solution in 350 ml of reverse osmosis water and then adjusted to pH 3.3 with 0.1 M HCl.

Then the Recombumin™ solution was recirculated through the tube with its filter matrix for 16 h at room temperature by using a pump at a flow rate of <5 ml/min. The porous matrix was finally rinsed with reverse osmosis water.

The surface protein content on the porous structure surface of the obtained matrix was determined by using Coomassie Brilliant Blue (BioRad, USA).

Example 16

The porous polyethylene matrix obtained according to Example 4 was perfused with a polyethyleneimine (Sigma)

solution, 10 mg/ml, over night at a flow rate of 5 ml/min in a closed circuit. Then, the porous matrix was rinsed with water.

The amount of primary amines on the porous structure surface of the obtained matrix was assayed as described in Example 3.

Direct Conjugation of Ligands

Example 17

The porous polyethylene matrix obtained according to Example 5 was conjugated with deoxycholate (DOC) by using an aqueous solution of WCCM. A solution of 300 ml 40% dimethylformamide (DMF) (Sigma) in water, which contained 1 mmol of sodium deoxycholate, was added to the porous polycarbonate with stirring while adjusting the pH with 0.3 M HCl to pH 4.8. A solution of 6 mM WCCM in DMF:water (1:1.8) was then added over a period of 10 min. The suspension was maintained at pH 4.8 for 3 h by the addition of 0.3 M HCl.

The DOC content on the porous structure surface of the obtained matrix was determined by using a Bile Acid Kit (Sigma).

Example 18

The porous polyethylene matrix obtained according to Example 3 was conjugated by using 12% glutardialdehyde in 0.15 M phosphate buffer, pH 7.0 for 24 h at room temperature. The matrix was washed with 0.15 M phosphate buffer and then anti CD14 antibodies (DAKO, Denmark) was added at a concentration of 1 mg/ml and incubated at 8° C. for 24 h. Subsequent reduction with sodium cyanoborohydride was performed in order to produce stable secondary amine linkages.

The antibody content on the porous structure surface of the obtained matrix was indirectly determined by means of UV spectroscopy of the antibody buffer solution before and after incubation with the porous matrix.

Example 19

The porous polyethylene matrix obtained according to Example 8 was washed with 0.15 M phosphate buffer and then a recombinant IL-1 receptor (Kineret, Amgen, USA) was added at a concentration of 1 mg/ml and incubated at 8° C. for 24 h. Subsequent reduction with sodium cyanoborohydride was performed in order to produce stable secondary amine linkages.

The IL-1 receptor content on the porous structure surface of the obtained matrix was indirectly determined by means of UV spectroscopy of the IL-1 receptor buffer solution before and after incubation with the porous matrix.

Example 20

The porous polyethylene matrix obtained according to Example 5 was conjugated by using 1.0% glutardialdehyde and 0.2 M phosphate buffer, pH 7.5. The matrix was incubated with this solution for 3 h. After washing with phosphate buffer the matrix was incubated in a solution of Polymyxin B sulphate (Sigma), 1 mg/ml, over night under recirculation. The matrix was finally washed with 0.1 M phosphate buffer, pH 7.4.

Example 21

The porous polyethylene matrix obtained according to Example 2 was conjugated with recombinant TNF-α receptor (Enbrel, Wyeth, UK) at a concentration of 5 mg/ml in 0.1 M 2-(N-morpholino)ethanesulfonic acid (MES) buffer (Sigma), pH 4.8. Thirty mg/ml of an aqueous solution of WCCM was added and the matrix was incubated over night at 8° C. The matrix was finally washed with 0.1 M phosphate buffer, pH 7.4.

The TNF-α receptor content on the porous structure surface of the obtained matrix was indirectly determined by means of UV spectroscopy of the TNF-α receptor buffer solution before and after incubation with the porous matrix.

Example 22

The porous polyethylene matrix obtained according to Example 3 was conjugated with an anti-human TNF-α antibody (Sigma) by using a 1.0% glutardialdehyde in 0.2 M phosphate buffer, pH 7.5. The matrix was incubated with the TNF-α antibody buffer solution for 3 h. After washing of the porous matrix with phosphate buffer, the anti-human TNF-α antibody (1 mg/ml) in phosphate buffer was added and incubated at room temperature for 6 h under recirculation at a flow rate of 1 ml/min. The matrix was finally washed with 0.1 M phosphate buffer, pH 7.4.

The TNF-α antibody content on the porous structure surface of the obtained matrix was indirectly determined by means of UV spectroscopy of the TNF-α antibody buffer solution before and after incubation with the porous matrix.

Example 23

The porous polyethylene matrix obtained according to Example 5 was conjugated with human bactericidal permeability increasing protein (BPI) (Wieslab, Sweden) at a concentration of 2 mg/ml in 0.1 M MES buffer, pH 4.8. An aqueous solution of WCCM was added to this matrix at a concentration of 15 mg/ml, and the matrix was incubated over night at 8° C. The matrix was finally washed with 0.1 M phosphate buffer, pH 7.4.

The BPI content on the porous structure surface of the obtained matrix was indirectly determined by means of UV spectroscopy of the BPI buffer solution before and after incubation with the porous matrix.

Example 24

The porous polyethylene matrix obtained according to Example 15 was incubated in a solution of DOC in 0.1 M MES buffer, pH 4.8, at a concentration of 1 mg/ml. Then an aqueous solution of WCCM was added, and the matrix was incubated over night at 8° C. The matrix was finally washed with 0.1 M phosphate buffer, pH 7.4.

The DOC content on the porous structure surface of the obtained matrix was determined as in Example 17.

Conjugation of Ligands with Spacer

Example 25

The porous polyethylene matrix obtained according to Example 3 and was activated with 1.2% glutardialdehyde in 0.2 M phosphate buffer, pH 7.0 for 24 h at room temperature. The matrix was washed with buffer and subsequently incubated for 24 h in 1,6-diaminohexane (DAH) (Sigma), 50 mg/ml, in 0.2 M phosphate buffer, pH 7.0. Thereafter, 10 mg/ml sodium cyanoborohydrid (Sigma) was added to the solution. The porous matrix was washed with 0.1 M phosphate buffer and then incubated in a solution of DOC (1 mg/ml) in 0.1 M MES buffer, pH 4.8. Then an aqueous solution of WCCM was added and the matrix was incubated over night at 8° C. The matrix was finally washed with 0.1 M phosphate buffer, pH 7.4.

The DOC content on the porous structure surface of the obtained matrix was determined as in Example 17.

Example 26

The porous polyethylene matrix obtained according to Example 5 was activated for 24 h at room temperature with 1.2% glutardialdehyde in 0.2 M phosphate buffer, pH 7.0. The matrix was washed with buffer and then incubated for 24 h with adipic dihydrazide (Aldrich) at a concentration of 10 mg/ml in 0.2 M phosphate buffer, pH 7.4. Then 10 mg/ml of sodium cyanoborohydrid (Sigma) was added to the solution.

The porous matrix was washed with 0.1 M phosphate buffer and then incubated with a solution of DOC at a concentration of 1 mg/ml in 0.1 M MES buffer, pH 4.8. Then an aqueous solution of WCCM was added, and the matrix was incubated over night at 8° C. The matrix was finally washed with 0.1 M phosphate buffer, pH 7.4.

The DOC content on the porous structure surface of the obtained matrix was determined as in Example 17.

Example 27

The matrix obtained according to Example 10 was conjugated with DOC by using an aqueous solution of WCCM. A water solution of 300 ml 40% DMF (Sigma), containing 1 mmol sodium deoxycholate, was added to the porous polycarbonate matrix while stirring. The pH of the suspension was adjusted to 4.8 with 0.3 M HCl. A 6 mM solution of WCCM in DMF:water (1:1.8) was added over a period of 10 min and the suspension was maintained at pH 4.8 for 3 h by the periodic addition of 0.3 M HCl. Then it was kept at room temperature for 24 h.

The DOC content on the porous structure surface of the obtained matrix was determined as in Example 17.

Example 28

The matrix obtained according to Example 14 was activated for 10 h at room temperature with 1.2% glutardialdehyde in 0.2 M phosphate buffer, pH 7.0, and then rinsed with excessive amounts of buffer. Polyethyleneimine (Sigma) at a concentration of 10 mg/ml in 0.1 M bicarbonate buffert, pH 8.0, was introduced into the porous matrix, and the matrix was incubated with the solution for 16 h.

The matrix was then washed with buffer and conjugated with DOC by using an aqueous solution of WCCM. A solution of 300 ml 40% DMF in water, containing 1 mmol of sodium deoxycholate, was added to the porous matrix while stirring. The pH was adjusted to 4.8 with 0.3 M HCl. A 6 mM solution of WCCM in DMF:water (1:1.8) was then added over a period of 10 min. The suspension was maintained at pH 4.8 for 3 h by the periodic addition of 0.3 M HCl. Then it was kept at room temperature for 24 h.

The DOC content on the porous structure surface of the obtained matrix was determined as in Example 17.

Example 29

The porous polyethylene matrix obtained according to Example 3 was activated for 24 h at room temperature with 1.2% glutardialdehyde in 0.2 M phosphate buffer, pH 7.0. The matrix was then washed with the buffer and incubated for 24 h with 1,6-diaminohexane (DAH) (Sigma) at a concentration of 50 mg/ml in 0.2 M phosphate buffer, pH 7.0. The porous matrix was then washed with 0.1 M phosphate buffer and incubated for 12 h at 8° C. as a suspension in a solution of TNF-α receptor (Enbrel, Wyeth, UK) at a concentration of 10 mg/ml in 0.1 M phosphate buffer, pH 7.4. Then a solution of sodium cyanoborohydrid (Sigma) at a concentration of 10 mg/ml was added to the suspension. The matrix was finally washed with 0.1 M phosphate buffer, pH 7.4.

The TNF-α receptor content on the porous structure surface of the obtained matrix was indirectly determined by means of UV spectroscopy of the TNF-α receptor buffer solution before and after incubation with the porous matrix.

Selective Binding and Separation of Blood Components

Cell separations were performed by allowing whole blood to pass through a filter of a matrix shaped as a disk and having an active surface of 0.02 m².

Figure 4:
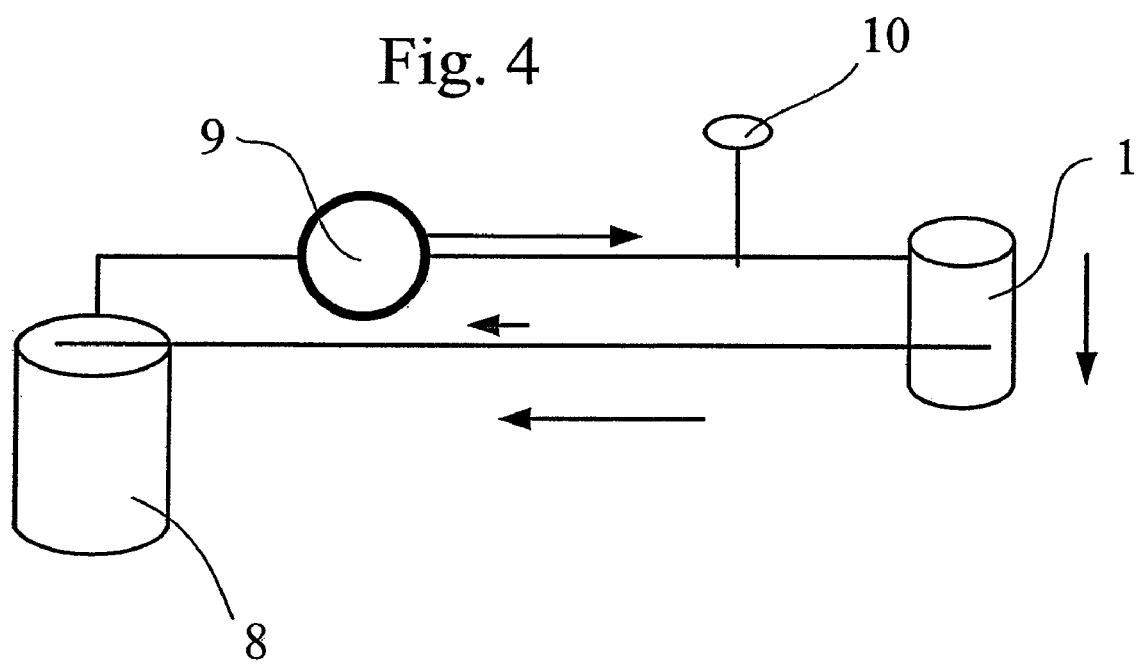
FIG. 4 is a schematic representation of a test system for the removal of endotoxins and cytokins according to the examples.

The removal of endotoxins and cytokins was performed with the test system shown in FIG. 4. A container 8, filled with up to 2 l of whole blood or plasma, was connected to a pump 9, a pressure monitor 10 and a filter device 1 with up to 40 matrix plates, i.e. an active surface of up to 7 m² being provided, which has a porosity between 70 and 130 micron.

Cell Separation

Example 30

A magnetic porous matrix comprising a mixture of polyethylene and magnetic ferrite (80% FeO, 20% BaO₂, Porex Technologies, Germany), which had a porosity of 100 micron, was used to separate leukocytes from whole blood by using specifically labeled anti CD45+ antibodies (MACS Antibody Microbeads; Miltenyi Biotec, Germany). After a magnetic labeling of the leukocytes with such antibodies, the blood was allowed to pass through the porous matrix.

Cell counting of leukocytes was performed by using an automatic Cell Counter, which after the separation showed a reduction of the leukocyte content in the blood of 90%.

Example 31

The surface of a matrix of porous cellulose diacetate (Tenite, Eastman Chemicals, USA), having a porosity of 200 micron and an active surface of 0.2 m², was used for separation of human fagocytating blood cells as neutrophils and monocytes. Human whole blood was collected in EDTA vacutainer tubes (B&D, UK) and the blood was allowed to pass through the porous matrix.

The reduction in the number of neutrophils and monocytes in the collected blood was 50% and 35%, respectively, as determined microscopically by differential cell counts in a Bürkner chamber by using Türks Reagent.

Cytokine Removal

Example 32

The matrix obtained according to Example 22, which had been coated with endotoxin removal groups, was used as porous disks in the test system shown in FIG. 4.

The elimination of TNF-α from whole blood was investigated after immobilizing polyclonal antibodies against TNF-α with glutardialdehyde onto the amino groups on the porous polymer structure. Production of TNF-α was induced by the addition of LPS to the blood and the activated whole blood was perfused over the immobilized filter in the device.

The amounts of TNF-α in whole blood (FIG. 5) was determined pre (♦) and post (v) the device by an enzyme immunoassay (Enzymimmuno-assay, Milenia Biotec GmbH, Germany) in order to study the uptake of TNF-α by the filter disks. As seen, a considerable reduction of pathological concentrations of TNF-α in whole blood could be obtained.

Endotoxin Removal

Example 33

The matrix obtained according to Example 25, i.e. a plasma modified polyethylene matrix having DOC thereon, was immobilized thereon via a spacer of diaminohexane, which first had been coupled to the matrix by glutardialdhyde and then to the deoxycholate by using carbodiimide. The obtained matrix was used as porous disks in the filter device of the system shown in FIG. 4.

The elimination of LPS from plasma was performed in a similar way as in Example 32.

The amount of LPS in plasma was determined by means of means of a Limulus Amebocyte Lysate assay (Endochrome-K, Charles River Laboratories Inc. USA) in the bulk at different time intervals during recirculation through the filter device.

In FIG. 6 the reduction of the amount of endotoxin (pg/ml) with time is shown. After a recirculation of 2 h the endotoxin load was reduced from 75 pg/ml at start to 15 pg/ml, which is the detection limit.

Example 34

The matrixes obtained according to Example 3 (non-immobilized amino groups) and Example 17 (immobilized DOC), respectively, were used as porous disks and compared with reference to their ability to eliminate LPS. A similar recirculation study as in Example 33 was performed with the difference that the LPS was dissolved in distilled water.

The elimination of LPS from the water solution was determined as shown in FIG. 4 while recirculating at a flow rate of 0.22 ml/min through each filter in a device of 10 ml.

In Table 1 below the values for elimination of LPS by the two matrixes from Example 3 and Example 17, respectively, are given as percentage of the initial LPS concentration after a recirculation of 120 min.

TABLE 1

|  | Example 3 | Example 17 |
|---|---|---|
| LPS elimination (%) | 81 | 96 |

The difference in degree of elimination between plasma (Example 34) and water (Example 35) can be explained by competitive interactions of proteins, LPS and ligand.

Combined Removal

Example 35

The matrixes obtained according to Example 19 and Example 29 were used for the combined removal of TNF-α and IL-1, respectively.

The two matrixes of different specificity were connected in serial in a closed loop test system of two filter devices as shown in FIG. 4. Whole blood in a container was kept at 37° C., activated by the addition of LPS, and introduced into the system. Sampling was performed at different time intervals simultaneous from the container and filter outlets for analysis of the cytokines.

The results showed for both matrixes a decrease in cytokine concentrations of 70% and 55% for TNF-α and IL-1β, respectively.

Table 2 below shows a summary of the versatile applicability and the considerable efficacy of the inventive method for selective binding and separation of different components from whole blood or a body fluid. For this purpose, different porous matrixes have been used as supports for the attachment of ligands, with or without a spacer. Thus, methods of immobilization have been performed with glutardialdehyd by using two terminal —NH$_2$ and with 1-ethyl-3(3-dimethylaminopropyl)carbodiimide with one terminal —NH$_2$ and one terminal —OH or —COOH, respectively. Silanization through aldehyde or amino functional silane coupling reagents for specific binding of amino groups, antibodies, enzymes, peptides, proteins have also been used, aldehyde groups reacting spontaneously with amines, peptides and proteins.

TABLE 2

| Porous matrix | Method | Spacer | Ligand | Component | Efficacy % |
|---|---|---|---|---|---|
| Polyethylene | — | HA | DOC | LPS | 80.1 |
| Polyethylene | — | Poly-Lys | DOC | LPS | 12.8 |
| Polyethylene | —NH$_2$ | DAH | DOC | LPS | 29.6 |
| Polyethylene | —NH$_2$ | — | DOC | LPS | 12.5 |
| Polyethylene | —NH$_2$ | DAH | Polymyxin B | LPS | 16.3 |
| Polyethylene | —NH$_2$ | DAH | Arginine | LPS | 14.3 |
| Polyethylene | —NH$_2$ | DAH | Recombumin | LPS | 18.3 |
| Polyethylene | —NH$_2$ | — | Anti-TNFα Ab | TNF-α | 63.2 |
| Polyethylene | Allyl-amine | PEI | DOC | LPS | 33.4 |
| Polyethylene | Allyl-amine | Poly-Lys | DOC | LPS | 85.5 |
| Polyethylene | —COOH | — | TNF-α Receptor | TNF-α | 59.2 |
| Polyethylene | —COOH | — | Interleukine-1 Receptor | IL-1 | 64.0 |
| Polyethylene | —COOH | — | Thrombomodulin | Thrombin | 70.8 |
| Polyethylene | —COOH | — | BPI | LPS | 91.2 |
| Polyethylene | —OH | Sil.ald. | TNF-α Receptor | TNF-α | 61.8 |
| Polyethylene | —OH | Sil.ald. | Interleukine-1 Receptor | IL-1 | 62.0 |
| Polyethylene | —OH | Sil.ald. | Thrombomodulin | Thrombin | 73.7 |
| Polyethylene | —OH | Sil.ald. | BPI | LPS | 89.3 |
| Polyethylene | HA | DAH | DOC | LPS | 29.6 |
| Polyethylene | Poly- | DAH | DOC | LPS | 73.3 |

TABLE 2-continued

| Porous matrix | Method | Spacer | Ligand | Component | Efficacy % |
|---|---|---|---|---|---|
| Polyethylene | Lys Recombumin | — | DOC | LPS | 20.8 |
| Polyethylene | —NH$_2$ | GDA | Anti CD 11b Ab | Granulocytes and monocytes | 50.2 |
| Polyethylene | —OH | Sil.ald. | Anti CD 11b Ab | Granulocytes and monocytes | 56.1 |
| Polycarbonate | — | Poly-Lys | DOC | LPS | 44.4 |
| Polycarbonate | —OH | Sil.Ald | TNF-α Receptor | TNF-α | 75.9 |
| Polycarbonate | —COOH | — | Thrombomodulin | Thrombin | 72.0 |
| Polyurethane | — | DAH | DOC | LPS | 30.2 |
| Polyurethane | — | DAH | Recombumin | LPS | 18.5 |
| Polyurethane | — | Poly-Lys | DOC | LPS | 14.8 |
| Polyurethane | — | Sil.Ald | TNF-α Receptor | TNF-α | 56.7 |
| Polyurethane | — | Sil.Ald | BPI | LPS | 88.0 |
| Silicone | — | Sil.Ald | TNF-α Receptor | TNF-α | 55.3 |
| Silicone | — | Sil.Ald | Thrombomodulin | Thrombin | 68.2 |
| Zeolite | — | Sil.Ald | TNF-α Receptor | TNF-α | 63.9 |
| Zeolite | — | Sil.—NH$_2$ | DOC | LPS | 48.3 |
| Zeolite | — | Sil.Ald | Interleukine-1 Receptor | IL-1 | 60.1 |
| Cellulose | CNBr | DAH | DOC | LPS | 28.5 |
| Cellulose | CNBr | Poly-Lys | DOC | LPS | 39.2 |
| PTFE | Allyl-amine | DAH | TNF-α Receptor | TNF-α | 73.0 |
| PTFE | —COOH | — | Interleukine-1 Receptor | IL-1 | 77.7 |

Abbreviations:
BPI = bactericidal permeability increasing protein;
DAH = 1,6-diamino-hexane;
DOC = deoxycholate;
EDC = 1-ethyl-3(3-dimethylaminopropyl)carbodiimide;
GDA = glutardialdehyde;
HA = hyaluronic acid;
IL-1 = Interleukin-1;
PEI = polyethyleneimine;
Recombumin = recombinant human albumin;
Sil.ald. = aldehyde functional silane coupling reagent;
Sil.—NH$_2$ = amino functional silane coupling reagent;
TNF-α = tumour necrose factor-α.

The invention claimed is:

1. A method for selectively eliminating at least one component from an aqueous solution, comprising:
   passing said aqueous solution through a rigid integral separation matrix without being excluded by said matrix, said matrix having a porous structure with a pore size ranging from 5 microns to 500 microns and an active surface ranging from 0.5 cm$^2$ to 10 m$^2$;
   binding at least one aqueous solution component by a bile acid moiety immobilized on said matrix;
   whereby said matrix is obtained by a process selected from the group consisting of: sintering, moulding, and foaming.

2. The method of claim 1, wherein said bile acid moiety is a deoxycholic acid moiety.

3. The method of claim 1, further comprising:
   coating or surface modifying said porous structure of said matrix in order to arrange said bile acid moiety at said porous structure.

4. The method of claim 1, wherein said matrix is made of a material selected from the group consisting of:
   metal, inorganic oxide, carbon, glass, ceramic, synthetic polymer, and a natural polymer, and combinations thereof.

5. The method of claim 1, wherein said matrix is made of a magnetic metal.

6. The method of claim 4, wherein a synthetic or natural polymer is coated onto said material.

7. The method of claim 6, wherein said synthetic polymer is selected from the group consisting of:
   a polyolefine, a vinylic polymer, a fluorine containing polymer, a polyacrylate, a polyamide, a polyimine, a polyethylenimine, a polystyrene, a polystyrene copolymer, a silicone rubber, a polyester, a polycarbonate, a polyurethane, a poly sulfonate, a polyglycol, a polyether, a polyalkyloxide, a copolymer thereof, and a hybrid thereof.

8. The method of claim 6, wherein said natural polymer is selected from the group consisting of:
   a polysaccharide, a polycarbohydrate, a polyamino acid, a polylactic acid, or a polyglycolic acid, a copolymer thereof and a hybrid thereof.

9. The method of claim 3, wherein said surface modification is selected from the group consisting of:
   electrodeposition, electroevaporation, plasma chemical deposition, deposition from an ion plasma flow, plasma polymerization, plasma enhanced surface polymer deposition, and chemical vapor deposition.

10. The method of claim 1, wherein a further ligand is immobilized on said matrix, and said ligand is selected from the group consisting of:
    a recombinant protein, a peptide, an antibody, a fragment of an antibody, a carbohydrate, a polysaccharide, a hormone, an antioxidant, a glycoprotein, a lipoprotein, a lipid, a fat soluble vitamin, a reactive dye, allantoin, uric acid, or polymyxin, and combinations thereof.

11. The method of claim 10, wherein at least one cross-linker is covalently coupled between said matrix and said ligand.

12. The method of claim 11, wherein said cross-linker is selected from the group consisting of:
a homobifunctional crosslinker, a heterobifunctional crosslinker, and a trifunctional crosslinker.

13. The method of claim 11, wherein said cross-linker is covalently coupled as a spacer between said matrix and said ligand.

14. The method of claim 13, wherein said spacer is selected from the group consisting of:
a silane, a diisocyanate, a glycolate, a polyethyleneglycol, a succinimidyl reagent, a dihydrazine, adipidic acid, a diamine, an amino acid, an oligoamino acid, a polyamino acid, a peptide, and a protein.

15. A device for selective binding and separation of at least one component from an aqueous solution, comprising:
a housing;
an inlet;
an outlet; and
at least one separation matrix, said matrix being rigid and integral for passing said aqueous solution there through, said matrix having a porous structure with a pore size ranging from 5 micron to 500 micron and an active surface ranging from 0.5 $cm^2$ to 10 $m^2$, and a bile acid moiety being immobilized on said matrix and being able to bind said at least one component, wherein said separation matrix has a porous structure obtained by a process selected from the group consisting of: sintering, moulding; and foaming.

16. The device of claim 15, wherein said bile acid moiety is a deoxycholic acid moiety.

17. The device of claim 15, wherein said separation matrix comprises several disks arranged one after the other in the flow direction so that the aqueous solution is arranged to pass one disk and then flow out over the entire surface of the next disk.

* * * * *